United States Patent [19]

Hammerton

[11] Patent Number: 4,702,102
[45] Date of Patent: Oct. 27, 1987

[54] DIRECT READOUT DISSOLVED GAS MEASUREMENT APPARATUS

[75] Inventor: Denis Hammerton, Wayland, Mass.

[73] Assignee: Polaroid Corporation, Cambridge, Mass.

[21] Appl. No.: 566,307

[22] Filed: Dec. 28, 1983

[51] Int. Cl.[4] .......................... G01N 7/00; B01D 53/22
[52] U.S. Cl. ........................................... 73/19; 55/158; 55/270; 73/741
[58] Field of Search ...................... 73/19, 23, 741, 863, 73/23; 55/16, 158, 270

[56] References Cited

U.S. PATENT DOCUMENTS

| | | | |
|---|---|---|---|
| 2,639,616 | 5/1953 | Tate | 73/741 X |
| 3,040,561 | 6/1962 | Wright | 73/19 X |
| 3,060,726 | 10/1962 | Weber | 73/19 |
| 3,279,241 | 10/1966 | Pement | 73/19 X |
| 3,451,256 | 6/1969 | Kolodney | 73/19 X |
| 3,452,585 | 7/1969 | Vilinskas | 73/19 |
| 3,529,459 | 9/1970 | Vilinskas | 73/19 X |
| 3,866,460 | 2/1975 | Pearce, Jr. | 73/19 |
| 3,871,228 | 3/1975 | Weiss | 73/19 |
| 3,949,593 | 4/1976 | Oertle | 73/19 |
| 4,015,478 | 4/1977 | Schmaus | 73/741 |
| 4,056,968 | 11/1977 | Winslow, Jr. | 73/19 |
| 4,092,844 | 6/1978 | Oertle et al. | 73/19 X |
| 4,366,700 | 1/1983 | Bouck | 73/19 |
| 4,404,284 | 9/1983 | Heider et al. | 73/19 X |

FOREIGN PATENT DOCUMENTS

| | | | |
|---|---|---|---|
| 3023 | 1/1982 | Japan | 73/19 |
| 684865 | 12/1952 | United Kingdom | 73/863.23 |

Primary Examiner—Robert Spitzer
Attorney, Agent, or Firm—John J. Kelleher

[57] ABSTRACT

Relatively compact apparatus for rapidly and continuously measuring the percentage of dissolved gas in a liquid. In one embodiment thereof, the apparatus includes a gas permeable tube or membrane closed at one end having its other end connected to a pressure sensor. The gas permeable tube is mounted on the apparatus housing such that it can be immersed in the liquid to be measured. During the measurement process, if the liquid contains less dissolved gas than the equilibrium quantity at atmospheric pressure, it will absorb gas from within the gas permeable tube thereby changing the internal tube-gas pressure. The percentage of dissolved gas is related to the extent of gas absorption by the liquid and the resulting internal tube-gas pressure after gas absorption is substantially complete. Rapid measurement of the percentage of dissolved gas is achieved by altering the combined internal volume of the gas permeable tube and the pressure sensor to produce an optimum minimum internal volume within the combined internal volumes. In another embodiment, a portion of the gas permeable tube is also exposed to atmospheric pressure. Vapor from the liquid being tested passing through the tube that would otherwise condense within same subsequently passes through that portion of the tube exposed to atmospheric pressure to thereby preclude such condensation and thereby avoid dissolved gas measurement errors that might otherwise be produced by such condensation.

2 Claims, 8 Drawing Figures

DIRECT READOUT DISSOLVED GAS MEASUREMENT APPARATUS

BACKGROUND OF THE INVENTION

The present invention relates to apparatus for measuring the percentage of dissolved gas in a liquid, in general, and to relatively compact apparatus for rapidly measuring dissolved gas percentages in liquids moving within a conduit or similar enclosure, in particular.

The presence of dissolved gas in a liquid can produce any number of unwanted conditions in various manufacturing industries. In, for example, the photographic industry, the presence of dissolved gas in a coating fluid can have a decidedly negative impact on a finished photographic product. During the process of coating photographic films, for example, coating fluids are often subjected to pressures well in excess of and well below atmospheric pressure. If the coating fluid contains a significant amount of dissolved gas and this dissolved gas containing liquid is subjected to a low enough negative pressure, the dissolved gas will come out of solution in the form of gas bubbles. Gas bubbles in a photographic film coating fluid creates voids in the coating fluid that shows up as spots or imperfections in a finished photographic print. If the presence of dissolved gas in a photographic film coating fluid can be timely determined, steps can be taken to either remove any resulting gas bubbles or to preferably prevent the occurence of such gas bubbles by subjecting the dissolved gas containing coating fluid to conventional degassing techniques.

Several different techniques are presently available for measuring the percentage of dissolved gas in a liquid. However, each of these techniques suffers from one or more shortcomings that render them either unsuitable, inadequate or less than desirable for the dissolved gas measurement task presented.

In many applications it is desirable to have the percentage of dissolved gas rapidly and continuously measured. However, some gas measurement techniques involve the time-consuming task of extracting a sample of the liquid to be tested and then transporting same to a laboratory where the amount of dissolved gas is determined by observing bubble formation in the liquid while the liquid is being subjected to negative and positive pressures. Other techniques either employ apparatus that is not compatible with the liquid to be tested in that it might introduce contaminants into the liquid or are not capable of measuring the type of gas that is dissolved in same. Still other techniques determine dissolved gas percentage by changing the basic character of the liquid such as by burning or oxidizing same. In order to prevent contamination, the liquid sampled in such instances is precluded from being returned to the main body of liquid after dissolved gas measurements have been completed. This technique can produce a significant waste of liquid if employed over an extended period of time.

In U.S. Pat. No. 3,871,228 to WEISS, apparatus is disclosed for measuring the total pressure of gas components present in a large body of water. The apparatus includes a hollow tube-shaped gas permeable member for immersion in said body of water that is coupled to a pressure sensor having the form of either a manometer or a low internal volume pressure gauge. In addition to the excessive quantity of tubing-shaped membrane, employed, which would make such an arrangement unsuitable for the measurement of a process liquid moving within a relatively small conduit, the combined internal volume of the tubing, pressure gauge and coupling means between same is excessive for rapid pressure measurement and if such apparatus is employed to measure the total pressure of gas components in a liquid that is warmer than said apparatus, liquid vapor permeating the membrane will condense into a liquid within said membrane, thereby precluding meaningful measurement of gas pressures within said warmer liquid.

The primary object of the present invention is, therefore, to provide apparatus for rapidly and continuously measuring the percentage of dissolved gas in a liquid moving within a conduit.

Another object of the present invention is to provide apparatus for measuring the percentage of dissolved gas in a liquid whose temperature is higher than that of the dissolved gas measuring apparatus.

A further object of the present invention is to provide apparatus for measuring the percentage of dissolved gas in a liquid that is relatively compact and chemically compatible with the liquid to be measured.

Other objects, features and advantages of the present invention will be readily apparent from the following description of the preferred embodiment thereof taken in conjunction with the accompanying drawings.

SUMMARY OF THE INVENTION

In accordance with the present invention, relatively compact apparatus is provided for rapidly and continuously measuring the percentage of dissolved gas in a liquid moving within a conduit. The apparatus includes a gas permeable membrane in the form of a thin-walled tube, closed at one end, having its other end connected to a pressure sensor. The tube is mounted on the apparatus housing such that it can be readily immersed in the liquid to be measured. During the measurement process, if the liquid contains less dissolved gas than the equilibrium quantity at atmospheric pressure, it will absorb gas from within the gas permeable membrane, thereby changing the internal tube-gas pressure. The percentage of dissolved gas is related to the extent of gas absorption by the liquid and the resulting internal tube-gas pressure after gas absorption is substantially complete. Rapid measurement of the percentage of dissolved gas is achieved by altering the combined internal volume of the gas permeable tube and the pressure sensor to produce an optimum minimum internal volume within the combination of both of these internal volumes. In another embodiment, rapid and continuous dissolved gas measurement of a relatively warm liquid is obtained by exposing a predetermined portion of the gas permeable tube to the surrounding atmosphere.

DESCRIPTION OF THE PREFERRED EMBODIMENTS

Figure 1:
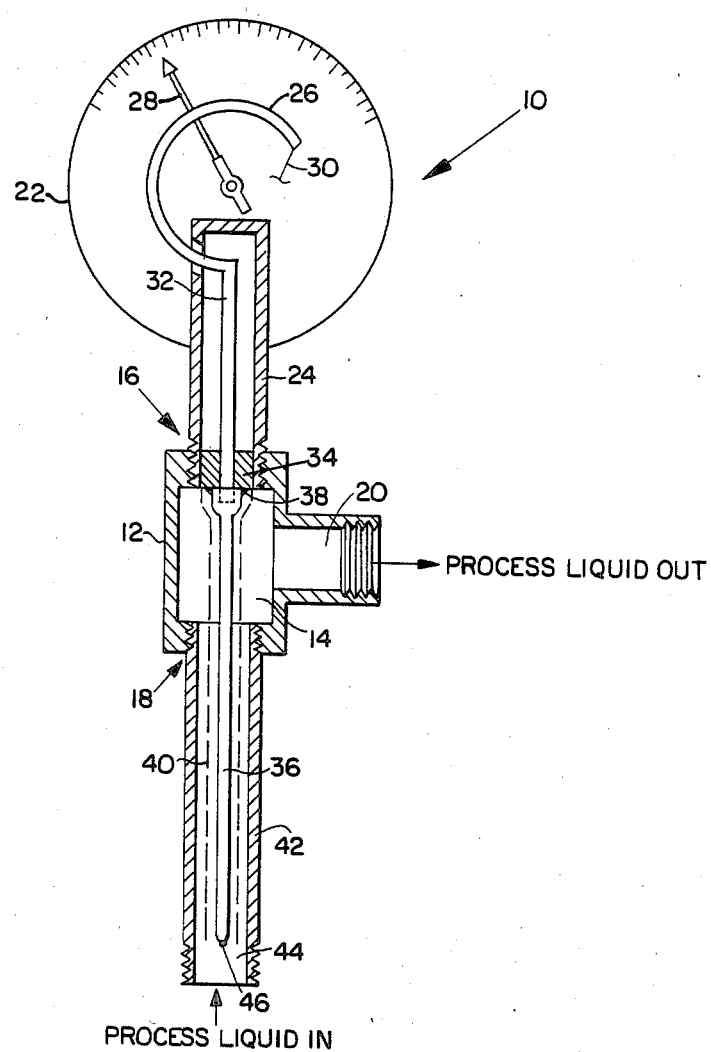
FIG. 1 is a schematic diagram in elevation and partly in section of apparatus employing a bourdon tube-type sensor and the rapid and continuous dissolved gas measurement of the present invention.

In FIG. 1 of the drawings, dissolved gas measurement apparatus 10 incorporating a preferred embodiment of the present invention, is depicted. Measurement apparatus 10 includes housing 12 completely enclosing spatial volume 14 having threaded openings 16, 18 and 20 therein. Bourdon tube pressure sensor 22 includes conduit 24 that supports sensor 22 together with related sensor components, said bourdon tube pressure sensor functioning in a fairly conventional manner. Pressure variations within C-shaped tube 26 causing pressure related movement thereof has such movement coupled to pressure indicating pointer 28 through path 30 and through additional movement coupling means that are not shown. Pressure responsive C-shaped tube 26 is coupled to the threaded end of conduit 24 by rigid tube 32, said rigid tube 32 projecting through and partially beyond flexible pressure seal 34. Silicone tubing 36, closed at one end, has the internal surface of its other end firmly engaging the outer surface of the projecting end of rigid tube 32, with a pressure-tight seal being formed between said tube 32 and silicone tube 36, in part, by sealant 38. Protective sheath 40, generally in the form of a well-perforated cylinder, completely surrounds silicone tube 36 and has one end thereof attached to the threaded end of support conduit 24. The threaded end of support conduit 24 is inserted into threaded opening 16 of housing 12 in a pressure-tight relationship and a threaded end of input conduit 42 is placed over sheath 40 and inserted into opening 18 in said housing 12, also in a pressure-tight relationship. Sheath 40 confines tubing 36 to the space within said sheath 40 to thereby prevent said tube from either completely blocking or excessively reducing the flow of process liquid through the above-mentioned conduits and housing of dissolved gas measurement apparatus 10. As noted above, protective sheath 40 is well perforated along its entire length. The reason for these perforations is to enable process liquid flowing through input conduit 42 to freely move toward and/or along the outer surface of gas permeable tube 36 for dissolved gas measurement purposes.

During the dissolved gas measurement process, liquid from a process liquid source (not shown) enters input conduit 42 through opening 44, flows into enclosed pressure-tight spatial volume 14 and then exits through output opening 20 toward a particular end use point (not shown). As the process liquid moves through input conduit 42 and housing space 14, at least a portion of said process fluid moves freely along the outer surface of gas permeable tube 36. If the liquid contains less dissolved gas than the equilibrium quantity of dissolved gas at atmospheric pressure it will absorb gas from within tube 36 thereby changing (lowering) the internal tube-gas pressure. The percentage of dissolved gas in said process liquid is related to the extent of gas absorption by said liquid and the resulting internal tube-gas pressure after gas absorption is substantially complete.

When measuring the percentage of a dissolved gas in a liquid in general and in a process liquid in particular, the more rapid the measurement can be made, the more timely can be any corrective action taken to change the percentage of dissolved gas to the desired or to an acceptable level if such a change is indicated. Presently available methods for measuring dissolved gas consume valuable time that necessarily precludes a rapid response to unwanted sudden changes in the percentage of dissolved gas. In the dissolved gas measurement apparatus described above and schematically illustrated in drawing FIG. 1, the excessive delay in obtaining dissolved gas measurement data associated with presently available measurement techniques, is avoided. As explained above, portions of the gas within tube 36 in said FIG. 1 will be absorbed by the liquid in which said tube is immersed to the extent that the amount of dissolved gas in said liquid deviates from the equilibrium quantity of dissolved gas at atmospheric pressure. As said gas is absorbed by the liquid from within tube 36 there will be an attendant drop in internal tube-gas pressure, also previously noted. The rate at which the gas pressure within tube 36 falls during the gas absorption process is primarily dependent upon the total volume of gas within tube 36 and sensor 22 in general, but more importantly, to the extent of "dead air space" within tube 36 and sensor 22, in particular. Dead air space is herein defined as that portion of the total volume of gas within tube 36 and pressure sensor 22 that is not immediately adjacent the relatively thin wall of gas permeable tube 36. The larger this dead air space, the longer it takes and/or the more difficult it is to produce a meaningful change in the gas pressure and an attendant pressure change indication, a pressure that is indicative of the percentage of dissolved gas in the liquid being measured.

In order to produce a meaningful change in tube gas pressure and the attendant indirect pressure sensor 22 indication of the percentage of dissolved gas in the liquid being measured as rapidly as possible, the total enclosed volume or space within gas pressure sensor 22 and gas permeable silicone tube 36 must be optimized. To optimize said total enclosed volume, pressure gauge 22, capable of measuring the range of gas pressures to be encountered and having the smallest available internal volume, is selected. Thin-walled gas permeable tube 36 preferably made of silicone rubber, having the largest external surface area to internal volume, is also selected. A liquid-tight seal is formed in free end 46 of tube 36 by conventional tube sealing means. Means for coupling the internal volume of tube 36 to the internal volume of C-shaped tube 26, such as rigid tube 32, is then provided, if such coupling means is necessary. If such coupling means is necessary, its internal volume should be minimized. The length of gas permeable tube 36 is then chosen such that its internal volume is approximately equal to twenty times the combined internal volume of C-shaped tube 26 and rigid coupling tube 32. It has been determined that by increasing the length of tube 36, the response time or the time required to obtain a fairly constant indication of gas pressure within tube 36 and therefore the percentage of dissolved gas in the liquid being measured, is reduced. However, it has also been determined that any increase in the length of tube 36 that increases the ratio of the internal tube volume of said tube to the internal volume of the pressure sensor plus any non-gas permeable coupling means beyond twenty-to-one will produce no meaningful reduction in the time required to obtain a fairly constant indication of dissolved gas indicating gas pressure within said gas permeable tube 36. Additional arrangements are described below for optimizing the total enclosed spatial volume within a pressure sensor, a gas permeable tube and any means necessary to interconnect these two components.

Figure 2:
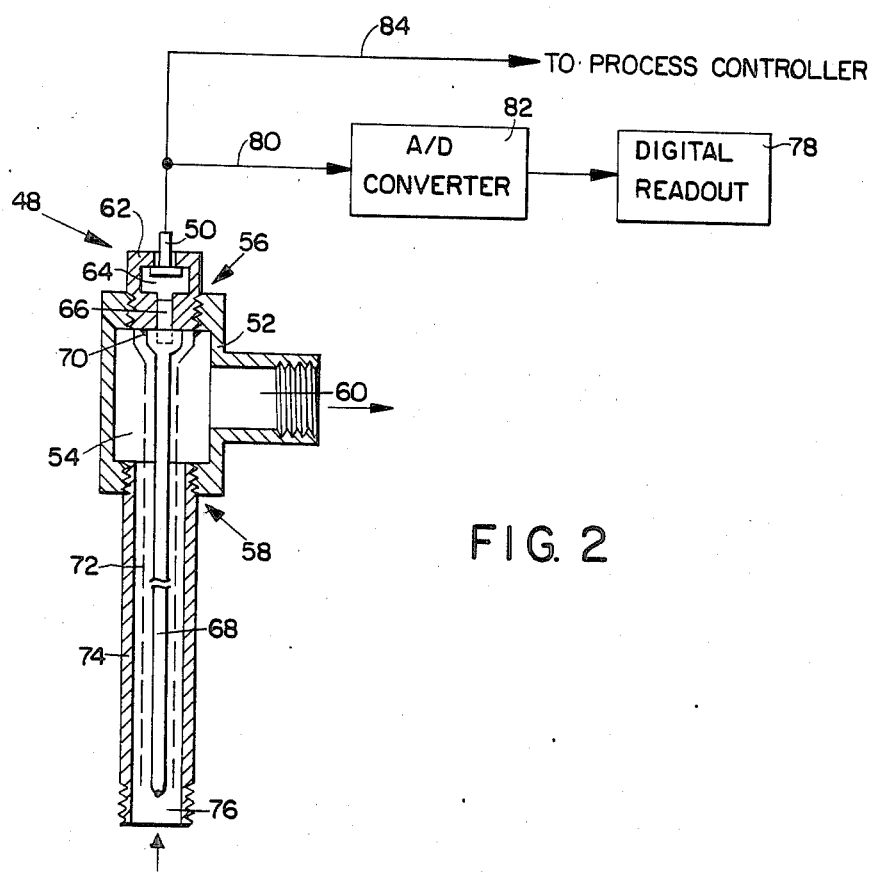
FIG. 2 is a schematic diagram, in elevation and section, of apparatus employing a piezoelectric-type sensor and the rapid and continuous dissolved gas measurement of the present invention.

In FIG. 2 of the drawings, dissolved gas measurement apparatus 48 incorporation piezoelectric-type pressure sensor 50 is schematically illustrated. Apparatus 48 includes gas measurement apparatus housing 52 completely enclosing spatial volume 54, said housing 52 having threaded openings 56, 58 and 60 therein. Pressure sensor 50 is mounted on piezoelectric sensor support housing 62 in a pressure-tight relationship. Gas movement into or out of spatial volume 64 within said support housing 62 as a result of changes in gas pressure takes place solely through projecting tube 66 at the threaded end of support housing 62, a tube that is in pressure-tight communication with said spatial volume 64. Silicone tubing 68, closed at one end, has the internal surface of its other end firmly engaging the outer surface of the projecting end of tube 66, with a pressure-tight seal being formed between the projecting end portion of tube 66 and silicone tube 68, in part, by sealant 70. Protective sheath 72, generally in the form of a well perforated cylinder, completely surrounds silicone tube 68 and has one end thereof attached to the threaded end of transducer support housing 62. The function of protective sheath 72 in dissolved gas measurement apparatus 48 is the same as that of protective sheath 40 in dissolved gas measurement apparatus 10 described above and schematically shown in drawing FIG. 1. The threaded end of transducer support housing 62 is inserted into threaded opening 56 of housing 52 in a pressure-tight relationship and a threaded end of input conduit 74 is placed over sheath 72 and inserted into opening 58 in said housing 52, also in a pressure-tight relationship.

With continued reference to FIG. 2, during the dissolved gas measurement process, liquid from a process liquid source (not shown) enters input conduit 74 through opening 76, flows into enclosed pressure-tight spatial volume 54 and then exits through output opening 60 toward a particular end use point (not shown). As explained above with respect to apparatus 10 of FIG. 1, process liquid flowing past the outer surface of gas permeable silicone tube 68 in the apparatus of FIG. 2, will absorb gas from within said tube 68 to the extent that said process liquid contains less dissolved gas than the equilibrium quantity of dissolved gas at atmospheric pressure, to thereby produce a gas pressure within tube 68 that is indicative of the percentage of dissolved gas in said process liquid. Piezoelectric-type pressure sensor 50 senses the resulting gas pressure within tube 68, generates an electrical signal representative of said resulting gas pressure and said signal is then routed to digital readout 78 through path 80 and analog-to-digital converter 82 to produce a visual indication of the measured gas pressure, and/or to a process controller (not shown) through path 84 for use in automatically controlling the percentage of dissolved gas in the measured process fluid or some other related function. In addition to the generation of an electrical signal representative of the gas pressure within gas permeable tube 68, a major difference between the dissolved gas measurement apparatus of FIG. 2 and that shown in drawing FIG. 1 is the dramatically smaller dead air space volume associated with measurement apparatus 48, consisting primarily of spatial volume 64 and the internal volume of coupling tube 66, over that associated with gas measurement apparatus 10 in said drawing FIG. 1. This smaller dead air space allows a shorter length of gas permeable tube to be employed to satisfy the preferred twenty-to-one volume criterion mentioned above and therefore, the size of gas measurement apparatus 48 in drawing FIG. 2 can be made substantially smaller than the gas measurement apparatus depicted in drawing FIG. 1.

In certain dissolved gas measurement applications it is desirous to have a dissolved gas meter, of the smallest possible size, commensurate with the required degree of gas measurement accuracy. Such a device is schematically shown in drawing FIG. 3A. Dissolved gas measurement device 85 illustrated in drawing FIG. 3A includes bourdon tube pressure sensor 86 that, with the exception of coupling tube 88, is identical in every respect and functions in the same manner as bourdon tube pressure sensor 22 that forms a part of dissolved gas measurement apparatus 10 shown in drawing FIG. 1. The end of coupling tube 88 extends approximately half-way into packing gland 90 that forms a pressure-tight seal between the outer surface of said tube 88 and the internal surface of support conduit 92. A gas permeable membrane in the form of silicone tube 94 that is closed at one end and open at the other, and having gas-displacing insert 96 positioned therein, has said opening end together with a portion of said insert 96 inserted into packing gland 90 and into butting engagement with the open end of coupling tube 88. Sealant 98 forms a pressure-tight seal between gas permeable tube 94 and packing gland 90. Hollow housing 100 includes threaded openings 102, 104 and 106. The threaded end of pressure sensor support conduit 92 is inserted into opening 102 in housing 100 in a pressure-tight relationship and a threaded end of input conduit 108 is inserted into opening 104 in said housing 100, also in a pressure-tight relationship. The percentage of dissolved gas in process liquid entering open end 110 of input conduit 108 and exiting through opening 106 of housing 100 is rapidly measured by dissolved gas measurement device 85 in the same way it is measured by apparatus 10 in drawing FIG. 1.

Figure 3C:
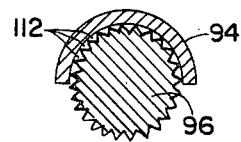
FIG. 3C is a cross-sectional view taken along the line 3C—3C in FIG. 3B.
Figure 3B:
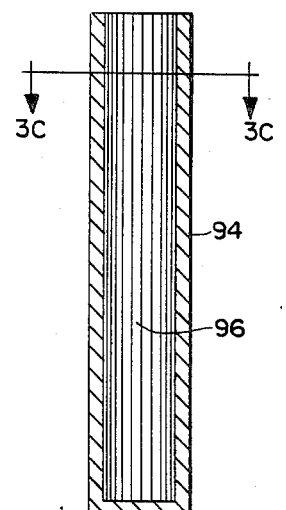
FIG. 3B is an enlarged elevational view, partly in section, of the volume displacing insert employed in the dissolved gas measurement apparatus of FIG. 3A.
Figure 4:
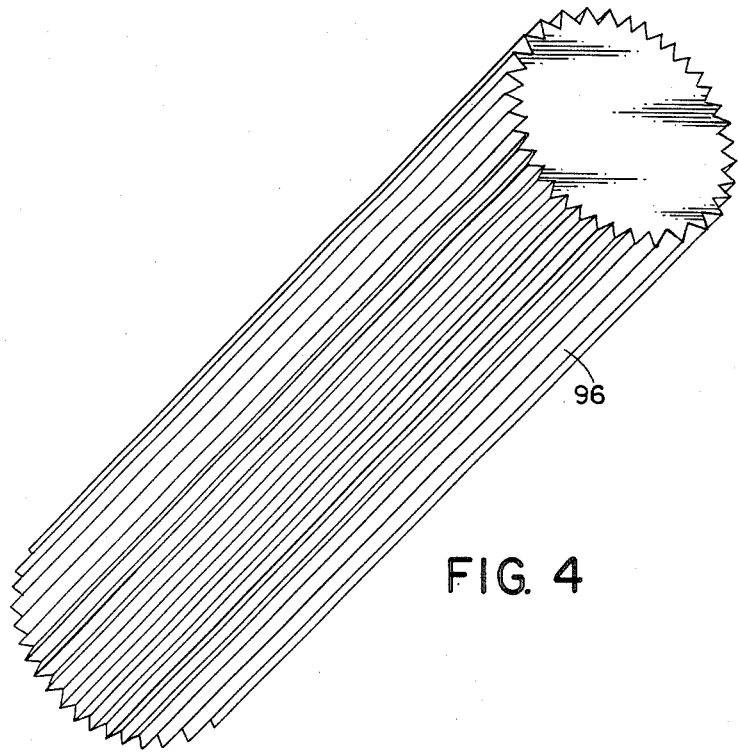
FIG. 4 is an enlarged perspective view of the volume displacing insert employed in the gas measurement apparatus shown in drawing FIG. 3A.

As explained above, the most significant factor in limiting the rate at which pressure within a gas permeable tube changes, is the extent of dead air space within said tube, its associated tube-gas pressure sensor and any necessary sensor-to-tube coupling. As stated above, the term "dead air space" in its broadest sense, includes tube gas that is not immediately adjacent the relatively thin wall of the gas permeable tube. Included within this just-described dead air space volume in the dissolved gas measurement apparatus of the present invention, is that volume of gas along the longitudinal center line of tube 94, a volume that is spaced from the wall of said tube 94. The air or gas within this central space or volume effectively acts as a gas reservoir in a manner similar to the quantity of gas or air within pressure sensor 86. This gas reservoir acts to prevent a rapid reduction in tube gas pressure and the attendant measurement of dissolved gas in the process liquid being measured. The relatively small size gas measurement apparatus 85 of FIG. 2 is optimized for the fastest measurement time possible for the dead air space volume within pressure sensor 86, the just-described dead air space within tube 94, and the volume within any required coupling between these components. This was accomplished by placing generally cylindrical insert 96 within tube 94 in the above-described manner. As shown in drawing FIGS. 3B, 3C and 4, insert 96 is a hollow cylinder closed at each end having regularly spaced V-shaped grooves in its outer surface in a direction that is parallel to the long axis of said insert 96. FIG. 3B is an enlarged sectional view, in elevation, of gas permeable tube 94 and volume displacing insert 96 located therein, FIG. 3C is a cross-sectional view taken on the line 3C—3C in said drawing FIG. 3B and FIG. 4 is an enlarged perspective view of hollow volume-displacing insert 96 positioned within said gas permeable tube 94. In drawing FIG. 3C, space or volume 112 between gas permeable tube 94 and the V-shaped surface of insert 96 is the total volume within tube 94 that interfaces or reacts with the process fluid in which said tube 94 is immersed. Spatial volume 112 is in direct communication with the internal volume of pressure sensor 86 through coupling tube 88. By including insert 96 within gas permeable tube 94, the total volume within apparatus 85 is optimized for its fastest possible dissolved gas measurement capability. The length of said tube is substantially shorter than that employed in, for example, the apparatus of drawing FIG. 1, and therefore this device can be employed where space is at a premium. Other shapes may be substituted for the V-shaped surface of insert 96 to obtain such internal volume optimization in gas measurement apparatus 85 or other equivalent dissolved gas measurement arrangements.

Figure 3A:
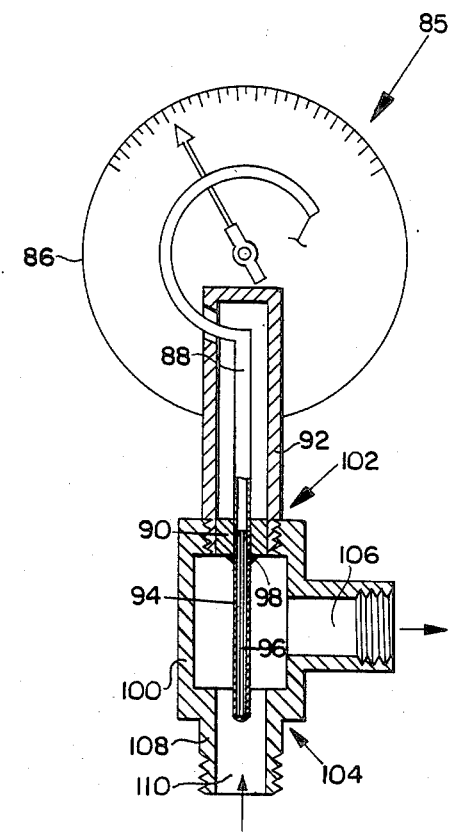
FIG. 3A is an extremely compact version of the dissolved gas measurement apparatus of FIG. 1.
Figure 5:
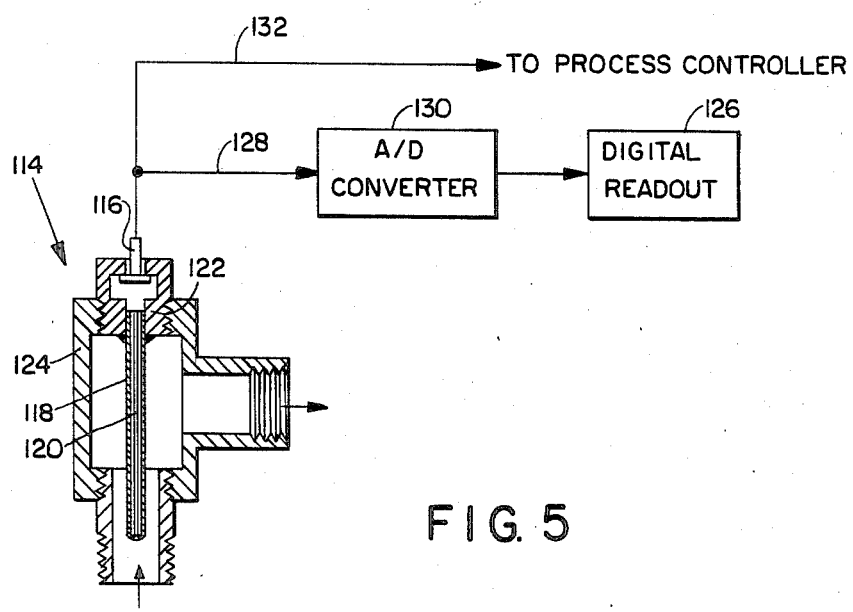
FIG. 5 is an extremely compact version of the dissolved gas measurement apparatus shown in drawing FIG. 2.

Dissolved gas measurement apparatus 114 shown in drawing FIG. 5 is primarily a combination of some of the parts of the two types of dissolved gas measurement apparatuses shown in drawing FIGS. 2 and 3A. Piezoelectric pressure sensor 116 and gas permeable tube 118 containing volume displacing insert 120, are mounted on pressure sensor housing 122 in the same manner that pressure sensor 50 is mounted on transducer housing 62 in the apparatus of FIG. 2 and the same manner that tube 94 containing volume displacing insert 96 is mounted in packing gland 90 in the apparatus of FIG. 3A, respectively. Transducer housing 122 is mounted on measurement apparatus housing 124 in the same pressure-tight manner that transducer housing 62 is mounted on measurement apparatus housing 52 in the apparatus of FIG. 2. An electrical signal generated by transducer 116 representative of the pressure within tube 118 is routed to digital readout 126 through path 128 and analog-to-digital converter 130 to produce a visual indication of the measured gas pressure and/or to a process controller (not shown) through path 132 for use in controlling the percentage of dissolved gas in the measured process fluid or some other related function. The combination of a piezoelectric-type pressure sensor and a gas permeable tube having a volume displacing insert therein results in a dissolved gas measurement device that is substantially smaller than either of those shown in drawing FIGS. 2 or 3A. In addition, the use of piezoelectric-type pressure sensor such as sensor 116 in drawing FIG. 5 results in a smaller magnitude of dead air space as defined herein and, therefore, results in a faster responding or indicating dissolved gas measurement meter.

Figure 6:
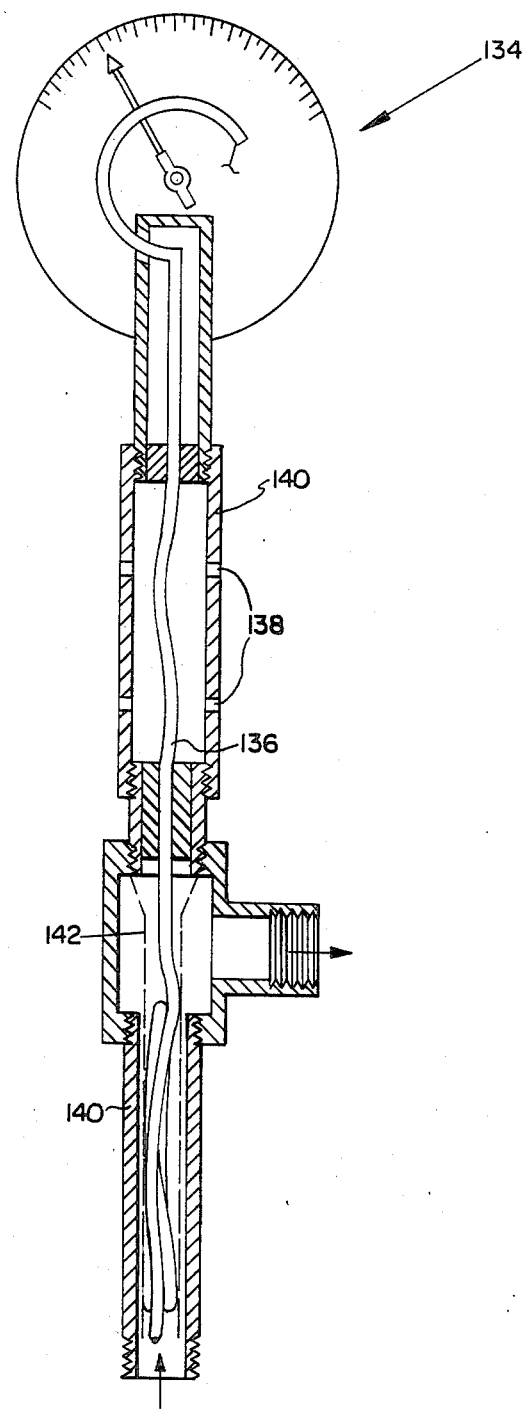
FIG. 6 is a schematic diagram in elevation and partly in section of apparatus that is capable of rapidly and continuously measuring dissolved gas in relatively warm liquids.

In some dissolved gas measurement applications, the temperature of the process fluid or other fluid to be measured is substantially warmer than the gas permeable tube employed in the above-described embodiments of the dissolved gas measurement apparatus of the present apparatus. If an attempt is made to measure the percentage of dissolved gas in a liquid under such a condition with the above-described dissolved gas measurement apparatus, process liquid vapors will very likely condense within the gas permeable tube, if the temperature differential is sufficient, and thereby render the dissolved gas measurement gauge inoperative. In order to preclude such a possibility, dissolved gas measurement device 134, shown in drawing FIG. 6, is provided with gas permeable silicone tube 136 having a portion of the exterior surface of same exposed to the atmosphere through vent openings 138 in vent housing 140. With the exception of vent housing 140 and gas permeable tube 136, dissolved gas measurement apparatus 134 is constructed in essentially the same manner as dissolved gas measurement apparatus 10 shown in drawing FIG. 1. By leaving a section of tubing 136 open to the atmosphere, process fluid vapors moving into tube 136 that might otherwise condense within same, can pass through the wall of said tube 136 and into the atmosphere through vents 138, thereby precluding such condensation. Obviously, if process liquid vapors can pass out of tube 136 through vent openings 138 in vent housing 140 air can and will simultaneously flow through the wall of gas permeable tube 136 in the opposite direction. In order to limit the extent to which air flows into tube 136 in this manner, the length of that portion of silicone tube 136 exposed to the atmosphere relative to the length of that portion of the tube immersed in the fluid to be measured must be such that the inward air flow does not preclude a valid dissolved gas measurement. The preferred arrangement was to make that portion of the tubing exposed to the atmosphere 4 inches in length while making that portion of the tubing immersed in the liquid to be measured 10 feet in length. In order to avoid an excessively long measurement device, in many applications the immersed end of tubing 136 can be folded within input conduit 140 and protective sheath 142.

It will be apparent to those skilled in the art from the foregoing description of my invention that various improvements and modifications can be made in it without departing from its true scope. The embodiments described herein are merely illustrative and should not be viewed as the only embodiments that might encompass my invention.

What is claimed is:
1. Apparatus for rapidly and continuously measuring the percentage of dissolved gas in a warm fluid moving within a conduit, comprising:
 a minimum internal volume pressure sensor;
 an elongated tube formed of a thin-walled gas-permeable membrane, said tube being closed at one end, having a maximum surface area to internal volume ratio and having its other end coupled to said sensor in a pressure-tight relationship with the combined internal volume of said pressure sensor and said elongated tube being altered to produce an optimum minimum internal volume within said combined volume; and means for supporting said dissolved gas measuring apparatus such that the external surface of one portion of said gas-permeable tube is exposed to air at atmospheric pressure where the area of said air-exposed external surface is large enough to permit fluid vapors from the measured fluid within said tube to pass through the tube wall and into the surrounding air while at the same time being small enough to limit the rate of air infiltration into said tube, to thereby preclude dissolved gas measurement errors resulting from infiltrating air and fluid vapors that might otherwise condense, within said gas permeable tube.

2. The apparatus of claim 1, wherein the length of that portion of the tubing for immersion in the liquid to be tested is approximately 10 feet and that portion of the length of tubing for exposure to atmospheric pressure is approximately 4 inches.

* * * * *